United States Patent
Alepee et al.

(10) Patent No.: US 10,869,654 B2
(45) Date of Patent: Dec. 22, 2020

(54) SET OF DISPOSABLE INSTRUMENTS FOR A SURGICAL OPERATION ON A PATIENT, AND METHOD FOR THE PRODUCTION OF SAID SET

(71) Applicant: One Ortho, Saint-Genis-Laval (FR)

(72) Inventors: Christophe Alepee, Lyons (FR); Thierry Guiton, Rouen (FR)

(73) Assignee: One Ortho, Saint-Genis-Laval (FR)

( * ) Notice: Subject to any disclaimer, the term of this patent is extended or adjusted under 35 U.S.C. 154(b) by 180 days.

(21) Appl. No.: 15/739,790

(22) PCT Filed: Jun. 23, 2016

(86) PCT No.: PCT/FR2016/051535
§ 371 (c)(1),
(2) Date: Dec. 26, 2017

(87) PCT Pub. No.: WO2017/001748
PCT Pub. Date: Jan. 5, 2017

(65) Prior Publication Data
US 2018/0199924 A1    Jul. 19, 2018

(30) Foreign Application Priority Data

Jun. 29, 2015 (FR) ...................... 15 56027

(51) Int. Cl.
*A61B 17/00* (2006.01)
*A61B 17/17* (2006.01)
(Continued)

(52) U.S. Cl.
CPC ............ *A61B 17/00* (2013.01); *A61B 17/154* (2013.01); *A61B 17/1764* (2013.01);
(Continued)

(58) Field of Classification Search
CPC ................ A61B 17/00; A61B 17/0023; A61B 17/00477; A61B 17/00482;
(Continued)

(56) References Cited

U.S. PATENT DOCUMENTS 4,947,867 A * 8/1990 Keeton ............. A61F 13/00059
128/846
8,540,700 B2 * 9/2013 Di Sessa ................ A61B 18/22
606/1

(Continued)

FOREIGN PATENT DOCUMENTS

EP        2510896        10/2012
WO    WO 2017/001748    1/2017

OTHER PUBLICATIONS

Rapport de Recherche Internationale et l'Opinion Ecrite [International Search Report and the Written Opinion] dated Sep. 2, 2016 From the Administration Chargée de la Recherche Internationale Re. Application No. PCT/FR2016/051535. (10 Pages).

*Primary Examiner* — Ahmed M Farah

(57) ABSTRACT

The invention relates to a set (1) of standard or tailor-made disposable instruments for a surgical operation on a patient, said set comprising at least two components (5) connected to each other by at least one connecting tab (6), which is connected separably to said components (5).

8 Claims, 3 Drawing Sheets

(51) Int. Cl.
*A61B 17/15* (2006.01)
*A61B 90/94* (2016.01)
*B33Y 10/00* (2015.01)
*B33Y 80/00* (2015.01)
*A61B 17/16* (2006.01)
*A61F 2/38* (2006.01)
*A61F 2/46* (2006.01)

(52) U.S. Cl.
CPC .......... *A61B 90/94* (2016.02); *A61B 17/1675* (2013.01); *A61B 17/17* (2013.01); *A61B 2017/0023* (2013.01); *A61B 2017/00526* (2013.01); *A61F 2/38* (2013.01); *A61F 2/461* (2013.01); *A61F 2/4684* (2013.01); *B33Y 10/00* (2014.12); *B33Y 80/00* (2014.12)

(58) Field of Classification Search
CPC ........ A61B 17/00486; A61B 17/00526; A61B 17/15; A61B 17/154; A61B 17/16; A61B 17/1675; A61B 17/17; A61B 17/1764; A61B 90/90; A61B 90/92; A61B 90/94; A61B 90/96; B33Y 10/00; B33Y 30/00; B33Y 80/00

USPC .................................. 606/1, 53, 79; 128/898
See application file for complete search history.

(56) References Cited

U.S. PATENT DOCUMENTS

| | | | |
|---|---|---|---|
| 2010/0217270 A1* | 8/2010 | Polinski ................ | A61F 2/0095 606/87 |
| 2011/0060341 A1* | 3/2011 | Angibaud ............ | A61B 17/155 606/89 |
| 2012/0109137 A1* | 5/2012 | Iannotti .............. | A61B 17/1728 606/87 |
| 2012/0116203 A1* | 5/2012 | Vancraen ............ | A61F 2/30942 600/407 |
| 2013/0018371 A1* | 1/2013 | Twomey ................ | A61B 17/28 606/41 |
| 2013/0184713 A1* | 7/2013 | Bojarski ................ | A61B 17/154 606/88 |
| 2013/0211531 A1* | 8/2013 | Steines ................ | A61F 2/4684 623/20.35 |
| 2015/0057702 A1 | 2/2015 | Edmondson et al. | |

* cited by examiner

SET OF DISPOSABLE INSTRUMENTS FOR A SURGICAL OPERATION ON A PATIENT, AND METHOD FOR THE PRODUCTION OF SAID SET

RELATED APPLICATIONS

This application is a National Phase of PCT Patent Application No. PCT/FR2016/051535 having International filing date of Jun. 23, 2016, which claims the benefit of priority of French Patent Application No. 1556027 filed on Jun. 29, 2015. The contents of the above applications are all incorporated by reference as if fully set forth herein in their entirety.

FIELD AND BACKGROUND OF THE INVENTION

The present invention relates to the technical sector of surgery, such as orthopedic surgery, and relates more particularly to a production method for disposable instrumentation constituted of at least two components, standard or tailor-made for a patient for performing a surgical procedure.

The invention also relates to all the disposable instruments as a set.

In surgery, for example orthopedic surgery, it is known to make disposable instruments, for example tailored to a specific patient. Instrumentation means any instrument necessary for performing a surgical procedure, for example for fitting and placing different orthopedic implants, such as a knee prosthesis.

The components that form the set of instruments are, for example, test implants, and instruments for fitting such as piercing guides, grippers or impactors. Said components are made of plastic by an additive production technique, such as by 3D printing.

Disposable means for single-use, for a single surgical procedure.

Additive production consists of producing, layer by layer, the components that form the instrumentation. This production technique allows a very large number of components to be made, for example tailor-made, for many patients, in a low production volume.

FIG. 1 represents, as an example, a production volume of a plurality of components tailored to distinct patients. This production volume is also known as "charge."

However, a first drawback related to this production technique of a plurality of components intended for different patients, in a low production volume, lies in the traceability of components for a patient, and in the risk of loss and/or mixing two components for two patients or from two batches of instruments of different sizes.

Indeed, producing disposable instrumentation with this technology allows the production of between 1 and 50 components for a single patient and, knowing that the components are produced for several patients at one time, it is highly possible to mix the components for two different patients or from two different batches of instruments. Said components may, certainly, be marked by a specific reference to the patient concerned, but the fact that these components are white does not help in reading these references and complicates traceability further.

To overcome this first drawback related to the traceability of components for each patient, it has already been envisaged to produce by an additive production technique and at the same time as the components, plastic boxes enclosing all the components for a single patient together, as illustrated in FIG. 2, commonly called a Sinter Box by machine producers.

This technique prevents mixing of the components during the production step, and also prevents losing small components. However, after the production step, it is useful to clean and process said components, by sanding or projection of microbeads to remove plastic powder residue from the production operations. To carry out this treatment, it is useful to open the plastic boxes in order to remove the components and treat them. The risk of losing or mixing the components from two patients or from two different batches are again present at that moment. This solution does not therefore ensure perfect component traceability up to the surgical procedure on the patient, and does not entirely remove the risk of losing or mixing two components from two patients or from two different batches.

Additive production consists of depositing on a table a layer of plastic powder, a few hundredths of a centimeter thick, and to fuse a useful section of this layer using a laser beam. The table then descends a few hundredths of a centimeter and a new layer of powder is deposited, then a useful section of this layer is fused. In this way the component is made layer by layer, and the layers are fused by a laser beam and added together.

In this manner, when an upper layer of powder is fused onto a previously fused lower layer, the quality of the upper fused layer is not degraded. However, when an upper layer is fused and it lies on a lower layer of unfused powder, a degradation effect occurs on the quality of dimensions and morphology of the upper fused layer.

In particular, when an upper layer of powder is deposited on a lower layer of non-fused powder, the upper layer of powder tends to lodge in the interstices of the lower layer of powder such that after fusion of the upper layer, this does not exhibit optimal quality, in particular at its edges, which become round, which can cause sizing problems.

This causes a second drawback when tailor-made components are to be made with extreme precision.

SUMMARY OF THE INVENTION

One of the goals of the invention is therefore to overcome the previously cited drawbacks by proposing a method for producing a set of standard or tailor-made disposable instruments for a surgical procedure on a patient, which ensures the traceability of said instruments until the surgical procedure on the patient. In other words, the production method according to the invention aims to prevent the loss of the components forming the set of instruments or to mix them with those for another patient or from another set of differently-sized instruments.

Another goal of the invention is to provide a method that can produce components with controlled positioning to ensure correct sizing of said components.

Another goal of the present invention aims to guarantee more legible marking to reference and identify the components for a specific patient.

To achieve this, the production method consists in producing, at the same time and by additive layer by layer production, components forming the set of instruments and connecting tabs, connected separably to the components, and connecting said components to form said set.

In this manner, the set of instruments only forms a single set comprising at least two standard or tailor-made components for a patient, connected to each other by connecting tabs that prevent loss of the components or mixing two components for two patients or from two sets of differently-sized instruments. After production, the components are treated and cleaned together, with their connecting tabs. It is only during the surgical procedure that the tabs, whose connection with the components is separable, are broken by the surgeon to detach said components one by one.

The invention also relates to controlling the positioning and orientation of the components produced relative to the succession of layers produced, which is very important for ensuring optimal quality in component parts requiring extreme precision and ensuring the correct sizing of said components.

The invention also relates to a set of standard or tailor-made disposable instruments for a surgical procedure on a patient. According to the invention, the set of disposable instruments comprises at least two components connected to each other by at least one connecting tab connected separably to said components.

Preferably, the connecting tab or tabs are flat and provided with an inscription, preferably through, identifying the references of the components and/or the patient for whom said components are intended.

Advantageously, the components are connected in the chronological order in which they must be used during the surgical procedure.

According to a specific embodiment, the components comprise at least one orifice, preferably shaped as a truncated cone or hemisphere, widening towards the external surface of the component, the base of said orifice being connected separably by a weakened area with a pointed end of a connecting tab.

In this manner, the components are attached to the connecting tabs reliably and form a sort of "cluster" of surgical components. Furthermore, the bond between the connecting tabs and the components is separable and prevents, after detachment, the formation of plastic pointed ends on the surface of the components that could tear the surgeon's gloves. Indeed, after separating the components and connecting tabs, any pointed ends formed by the fact of breaking said connecting tabs are hidden inside the orifices of said components.

BRIEF DESCRIPTION OF THE SEVERAL VIEWS OF THE DRAWINGS

Further characteristics and advantages of the invention will become apparent from the description provided below, which is for reference only and is in no way limiting, with reference to the accompanying figures, wherein.

DESCRIPTION OF SPECIFIC EMBODIMENTS OF THE INVENTION

Figure 1:
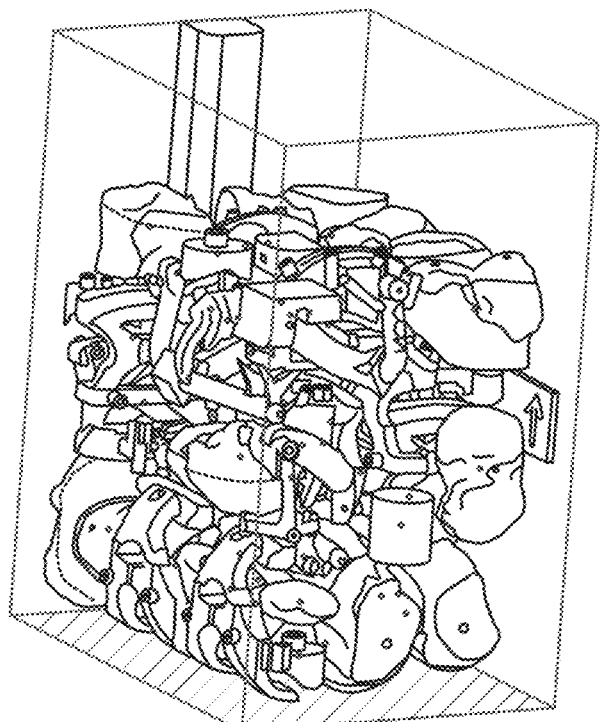
FIG. 1 is a schematic view in perspective illustrating a production volume, in accordance with the prior art, of a plurality of components tailored for distinct patients.
Figure 2:
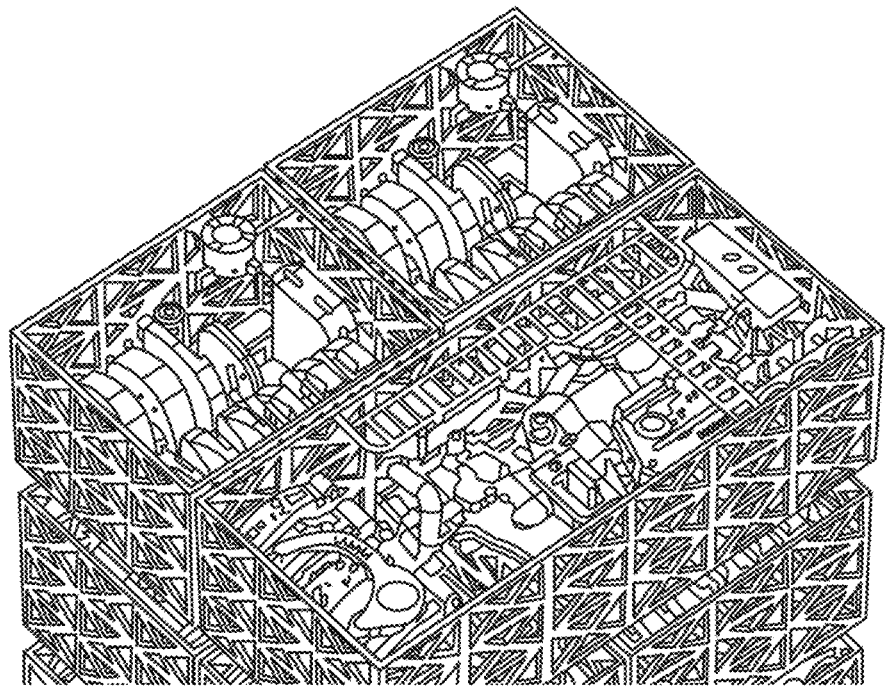
FIG. 2 is a schematic view in perspective illustrating the production technique of the prior art consisting in producing plastic boxes enclosing all the components for a single patient.
Figure 3:
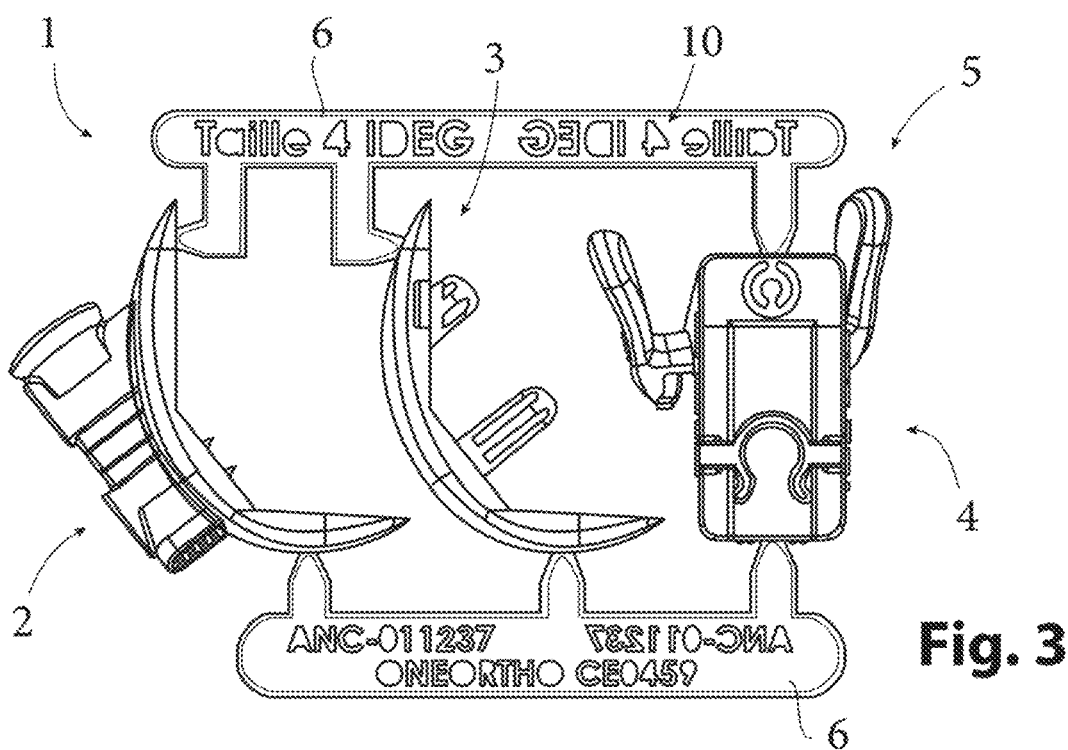
FIG. 3 is a schematic view from the front illustrating a set of disposable instruments according to the invention.
Figure 4:
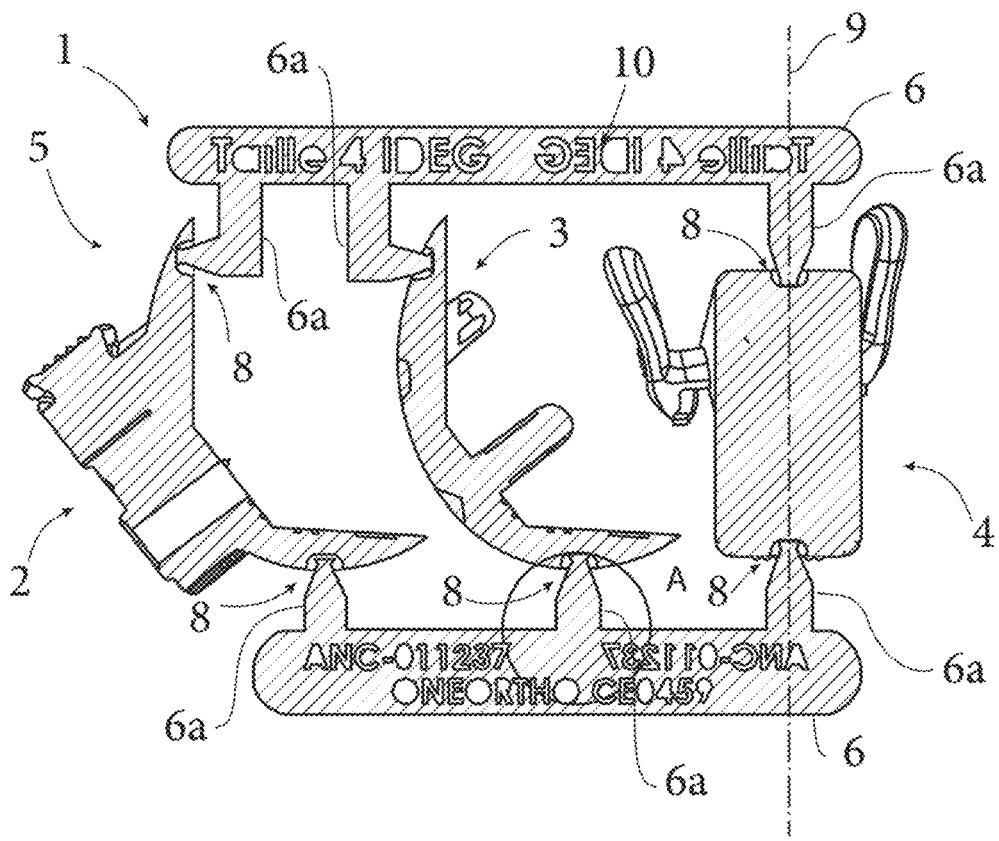
FIG. 4 is a schematic view similar to that of FIG. 3, the set of disposable instruments being shown in a lengthwise view.

The invention relates to a method for producing plastic, standard or tailor-made surgical instruments for a surgical procedure on a patient, for example comprising components of a single size, such as test implants, fitting instruments, such as cutting or piercing guides, grippers, or impactors.

The invention consists in producing the components that form the set of instruments by additive production, layer by layer, for example using a 3D printer. The components obtained are for single-use and have a relatively low cost price.

The components are made layer by layer, at the same time as connecting tabs, connected separably to said components, and arranged such that said components are connected to form a single set of components tailored for a single patient or a single set of components of a single size. This technique prevents the components from being lost and/or mixed with those of another patient or from another batch of differently-sized instruments.

These components, tailored to a specific patient, remain connected together during the cleaning and treatment step that follows production, and in particular until they are used in the operating theater. The components for a single set are intended to be separated from the connecting tabs by the surgeon himself. Preferably, the components are connected to each other in the chronological order in which they must be used during the surgical procedure, and preferably also oriented to ensure optimal sizing of said components.

With reference to FIGS. 3 to 6, the set of disposable instruments, referenced (1) made according to the invention comprises three components (5) for fitting a knee prosthesis, including a piercing guide (2), a test implant (3) and a gripper (4) for an impactor. Said components (5) are aligned and connected by two connecting tabs (6) arranged either side of the set of components (5). Each component (5) is connected to two connecting tabs (6) by separable bonds (7). For this purpose, each component (5) comprises two orifices (8) shaped as a truncated cone or hemisphere that widen towards the external surface of the component (5), each arranged on the component (5) near a connecting tab (6).

Figure 5:
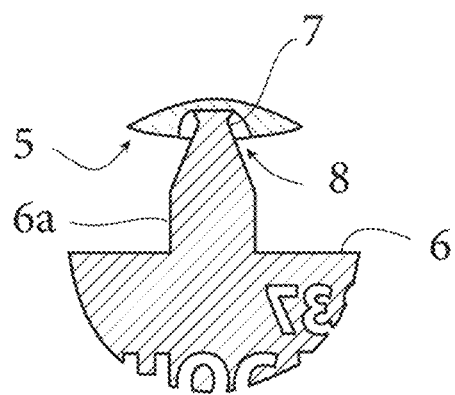
FIG. 5 is a detailed lengthwise cross-section view illustrating the separable bond between a pointed end of a connecting tab and a surgical component.

More precisely, and with reference to FIG. 5, the base of each orifice (8) is connected separably by a weakened area, in particular with small dimensions, with a pointed end of a connecting tab (6). In the example illustrated, each connecting tab (6) comprises three parts (6a) that extend in the direction of the components (5) whose ends are pointed and are connected separably inside the orifices (8).

Preferably, the orifices (8) arranged on a single component (5) are aligned along a single generatrix to facilitate the detachment of said component (5) Indeed, to detach said component (5), it suffices to turn it around the axis (9) of the generatrix.

Figure 6:
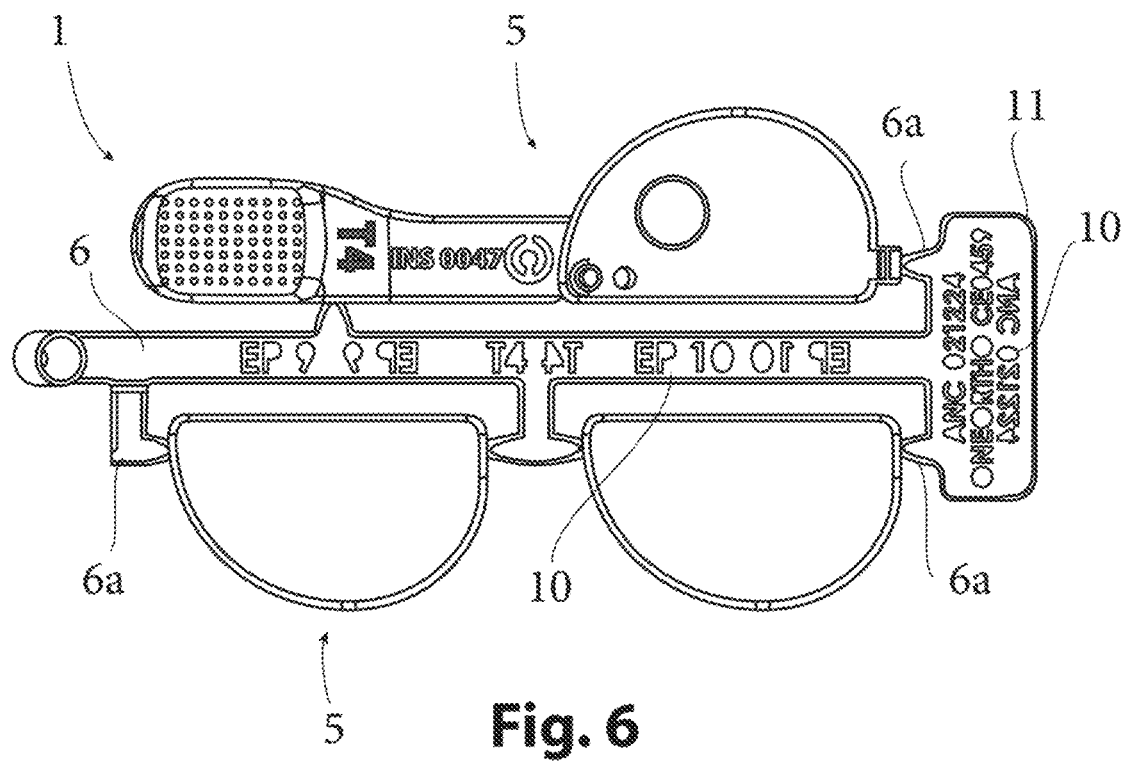
FIG. 6 is a schematic view similar to that of FIG. 3, the set of disposable instruments being illustrated from above.

Traceability is therefore improved because it is now possible to track the components (5) for a single patient from their production to their use. To further facilitate the traceability of said components (5), the connecting tab or tabs (6) comprise inscriptions (10) that identify the references of components (5) and/or the patient for whom they are intended. The connecting tabs (6) are advantageously flat to facilitate inscription and said inscriptions (10) preferably cross through the thickness of the connecting tab (6) to facilitate reading said inscriptions (10). With reference to FIG. 6, the invention also provides during production, areas (11) called "labels" that can receive extra identification inscriptions (10).

The invention then allows the components (5) for a single patient to be connected. It is also possible to check and control the positioning and orientation of the components (5) in the set (1) according to the invention. Indeed, as stated, the components (5) may be arranged in the chronological order in which they must be used during the surgical procedure, but they may also be oriented so as to position the faces not requiring very great precision orthogonally relative to the incident laser beam for the fusion. Accordingly, the sizing of components (5) is optimal and extreme precision of said components (5) can be ensured.

It is clear from the above, the invention provides a method for producing a set (1) of disposable instruments and the set (1) of standard or tailor-made instruments as such, for a surgical procedure of a patient, which ensures traceability of said instruments until the surgical procedure on the patient, and preventing loss of the components (5) that form the set (1) of instruments or mixing them with those of another patient or from another set of differently-sized instruments, while controlling the orientation of the components (5) to ensure their correct sizing. The invention also guarantees more legible marking to reference and identify the components (5) for a specific patient.

What is claimed is:

1. A set of disposable instruments for a surgical procedure on a patient, wherein the set comprises at least two components connected by at least one connecting tab connected separably to said components, wherein each component comprises at least one orifice, and wherein a base of each at least one orifice is connected separably to a pointed end of a connecting tab, forming a weakened area.

2. The set of disposable instruments according to claim 1, wherein the connecting tab or tabs are flat and provided with an inscription identifying the references of the components and/or the patient for whom said components are tailored.

3. The set of disposable instruments according to claim 2, wherein the inscription crosses through an entire thickness of the connecting tab.

4. The set of disposable instruments according to claim 3, wherein the components are connected in the chronological order in which the components must be used during the surgical procedure.

5. The set of disposable instruments according to claim 2, wherein the components are connected in a chronological order in which the components must be used during the surgical procedure.

6. The set of disposable instruments according to claim 1, wherein the components are connected a chronological order in which the components must be used during the surgical procedure.

7. The set of disposable instruments according to claim 1, wherein the orifices are shaped as a truncated cone or hemisphere and widen towards the external surface of the component.

8. A method for producing a set of disposable instruments for a surgical procedure on a patient, the method comprising:
   making, at the same time and by additive production layer by layer, components forming the set of instruments and connecting tabs, connected separably to the components, and
   connecting said components together said set,
   wherein each component comprises at least one orifice, and wherein the connecting step comprises connecting a base of each at least one orifice separably to a pointed end of a connecting tab, forming a weakened area.

* * * * *